(12) United States Patent
Misteli et al.

(10) Patent No.: US 9,617,599 B2
(45) Date of Patent: Apr. 11, 2017

(54) METHOD FOR DETECTION OF CANCER BASED ON SPATIAL GENOME ORGANIZATION

(75) Inventors: Thomas A. Misteli, Garrett Park, MD (US); Karen Meaburn, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/062,247

(22) PCT Filed: Sep. 3, 2009

(86) PCT No.: PCT/US2009/055857
§ 371 (c)(1),
(2), (4) Date: Mar. 28, 2011

(87) PCT Pub. No.: WO2010/028125
PCT Pub. Date: Mar. 11, 2010

(65) Prior Publication Data
US 2011/0183334 A1 Jul. 28, 2011

Related U.S. Application Data

(60) Provisional application No. 61/094,318, filed on Sep. 4, 2008.

(51) Int. Cl.
*C12Q 1/68* (2006.01)
(52) U.S. Cl.
CPC ...... *C12Q 1/6886* (2013.01); *C12Q 2600/112* (2013.01)

(58) Field of Classification Search
None
See application file for complete search history.

(56) References Cited

U.S. PATENT DOCUMENTS

2002/0068709 A1* 6/2002 Orum et al. .................. 514/44

OTHER PUBLICATIONS

Wiech. Histochem Cell Biol. 2005. 123: 229-238; p. 230.*
Conner. Breast Cancer Research and Treatment. 2003. 78: 159-165.*
Meaburn. The Journal of Cell Biology. 2009. 187(6): 801-812.*
Ransohoff. Nature Reviews Cancer. 2004. 4: 309-314.*
Lee. Journal of Clinical Endocrinology and Metabolism. 2001. 86(2): 913-920.*
Milde-Langosch. Breast Cancer Research and Treatment. 2004. 86: 139-152.*
Pick. Cancer Res. 2007. 67: 2932-2937.*
Liu. Int J Gynecol Cancer. 2007. 17(6): 1293-1299.*
2014 Procedure for Subject Matter Eligibility Analysis of Claims Reciting or Involving Laws of Nature/Natural Principles, Natural Phenomena, and/or Natural products. USPTO. Mar. 2014.*

(Continued)

*Primary Examiner* — Joseph G Dauner
(74) *Attorney, Agent, or Firm* — Leydig, Voit & Mayer Ltd.

(57) ABSTRACT

The invention provides methods of detecting abnormal cells in a sample using the radial position of one or more genes within the nucleus of a cell, as well as a kit for detecting abnormal cells using such methods. The invention also provides methods of identifying gene markers for abnormal cells using the radial position of one or more genes within the nucleus of a cell.

18 Claims, 7 Drawing Sheets

(56) References Cited

OTHER PUBLICATIONS

Akhtar et al., "The nuclear envelope and transcriptional control," *Nature Reviews: Genetics*, 8 (7), 507-517 (2007).
Alvarez et al., "Context-dependent transcription: all politics is local," *Gene*, 313, 43-57 (2003).
Cremer et al., "Inheritance of gene density-related higher order chromatin arrangements in normal and tumor cell nuclei," *J. Cell Biol.*, 162 (5), 809-820 (2003).
Finlan et al., "Recruitment to the nuclear periphery can alter expression of genes in human cells," *PLos Genetics*, 4 (3), e100039, 1-14 (2008).
Meaburn et al., "Locus-specific and activity-independent gene repositioning during early tumorigenesis," *J. Cell Biol.*, 180 (1), 39-50 (2008).
Meaburn et al., "Spatial genome organization in the formation of chromosomal translocations," *Seminar in Cancer Biology*, 17 (1), 80-90 (2007).
Misteli, "Beyond the Sequence: Cellular Organization of Genome Function." *Cell*, 128 (4), 787-800 (2007).
Reddy et al., "Transcriptional repression mediated by repositioning of genes to the nuclear lamina," *Nature*, 452 (7184), 243-247 (2008).
Smith et al., "SUSAN—A New Approach to Low Level Image Processing," *Int'l. J. Computer Vision*, 23 (1), 45-78 (1997).
Takizawa et al., "Allele-specific nuclear positioning of the monoallelically expressed astrocyte marker GFAP," *Genes & Development*, 22 (4), 489-498 (2008).
Meaburn et al. "Tissue-of-origin-specific gene repositioning in breast and prostate cancer," *Histochem Cell Biol* 145: 433-446 (2016).

* cited by examiner

Fig. 4
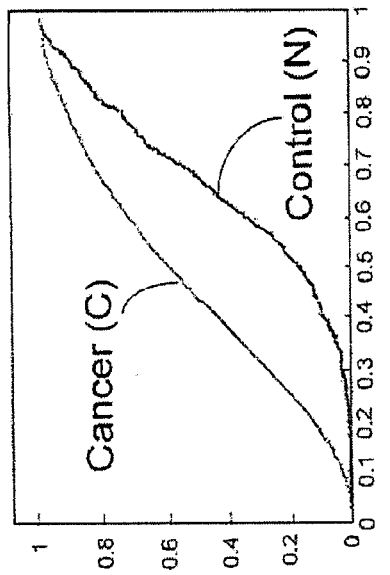
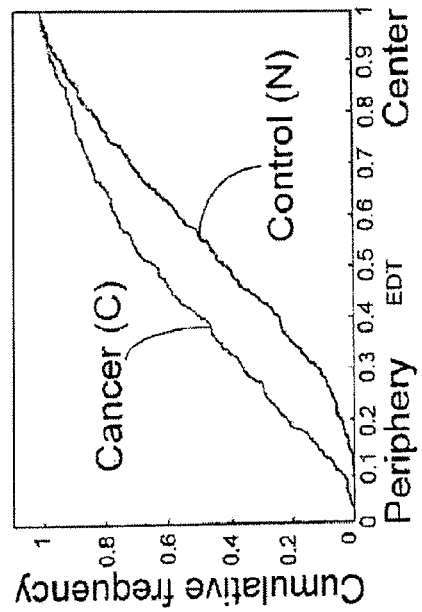

METHOD FOR DETECTION OF CANCER BASED ON SPATIAL GENOME ORGANIZATION

CROSS-REFERENCE TO RELATED APPLICATIONS

This patent application is a U.S. National Phase of International Patent Application No. PCT/US09/55857, filed Sep. 3, 2009, which claims the benefit of U.S. Provisional Patent Application No. 61/094,318, filed Sep. 4, 2008, which are incorporated by reference.

BACKGROUND OF THE INVENTION

Cancer is a leading cause of death worldwide. Survival rates for many cancers can be improved by early detection and treatment. Some patients and physicians disfavor available early detection methods due to invasiveness and/or perceptions of unreliability. More reliable methods of early detection are desired, as are less invasive methods of detection.

Ideal cancer diagnostics could be used in identifying a wide range of cancers, including solid tumor malignancies as well as hematological malignancies. Diagnostics capable of detecting precancerous cells are also desirable.

BRIEF SUMMARY OF THE INVENTION

Genes are non-randomly arranged within the cell nucleus. It has been surprisingly found that in abnormal cells, such as in cancers, the spatial organization of the genome is altered. Specifically, in some abnormal cells, the position of a gene relative to the nuclear center and/or the nuclear membrane, also called the radial position, differs from the position of the corresponding gene in a normal cell. Advantageously, detection of such difference is not limited to evaluation of mitotic chromosomes.

In an embodiment, the invention provides a method of detecting abnormal cells in a sample, the method comprising: (a) obtaining a sample comprising one or more cells from a subject, wherein one or more cells in the sample has a nucleus, and wherein each nucleus has a nuclear center and a nuclear membrane; (b) identifying the position of one or more genes within the nucleus relative to the nuclear center and/or nuclear membrane; and (c) comparing the position of the one or more genes with a positive and/or negative control; wherein a statistically significant difference in the position of the one or more genes as compared to a negative control, or a lack of statistically significant difference in the position of the one or more genes as compared to a positive control indicates the presence of abnormal cells.

In another embodiment, the invention also provides a method for identification of gene markers for abnormal cells, the method comprising: (a) obtaining a test sample comprising one or more abnormal cells from a subject, wherein one or more cells in the sample has a nucleus, and wherein each nucleus has a nuclear center and a nuclear membrane; (b) obtaining a control sample comprising one or more normal cells from a subject, wherein one or more cells in the sample has a nucleus, and wherein each nucleus has a nuclear center and a nuclear membrane; (c) identifying the position of one or more genes within the nucleus relative to the nuclear center and/or nuclear membrane; and (d) comparing the position of the one or more genes from the test sample with the corresponding position of the one or more genes from the control sample; and (e) determining the statistical significance of a difference in the position of the one or more genes from the test sample as compared to the control sample; wherein a gene having a statistically significant difference in position in the test sample as compared to the control sample is identified as a gene marker for abnormal cells.

In another embodiment, the invention also provides a kit for detecting abnormal cells in a sample, the kit comprising: (a) a labeled DNA probe for each of one or more genes selected from the group consisting of HES5, HSP90AA1, TGFB3, ERBB2, FRA2 (also known as FOSL2), CSF1R, MYC and AKT1; (b) instructions for measurement of the position of one or more genes in the sample, and interpretation of the results.

BRIEF DESCRIPTION OF THE SEVERAL VIEWS OF THE DRAWING(S)

FIG. 1 depicts P value comparisons of radial distributions of BCL2, CCND1, CSFR1, ERBB2, FRA2 (FOSL2), HES5, HEY1, TGFB3, and VEGF in non-cancerous samples N1-N5. Radial distributions were evaluated for each of N1 and N5, and paired comparisons were made. For each paired sample indicating P>0.01, the radial distributions were statistically the same at a significance of P>0.01.

FIG. 4A is a plot of the cumulative frequency (y-axis) of the radial position (x-axis) of AKT1 for an individual cancer sample and an individual normal control sample along with statistical analysis of seven cancerous samples and three non-cancerous control samples.

FIG. 4B is a plot of the cumulative frequency (y-axis) of the radial position (x-axis) of ERBB2 for an individual cancer sample and an individual normal control sample along with statistical analysis of seven cancerous samples and three non-cancerous control samples.

Figure 5:
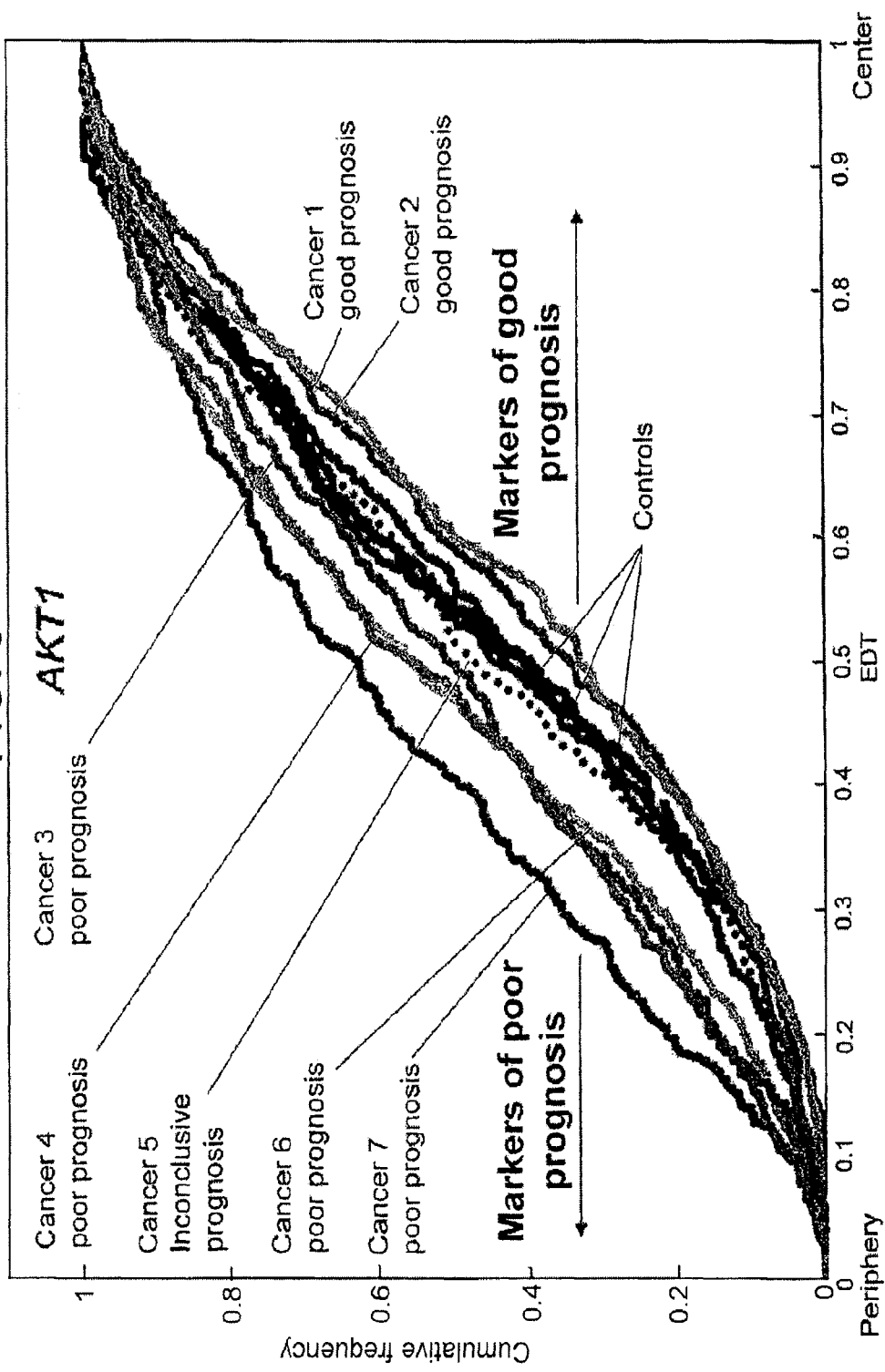

FIG. 5 is a plot of the cumulative frequency (y-axis) of the radial position (x-axis) of AKT1 for seven cancerous samples and three non-cancerous control samples. Samples C3, C4, C6, and C7 are identified in a common positional group. Samples C1 and C2 are identified in a common positional group. Control samples are identified as a common positional group. Sample C5 is identified separately due to its alignment with the control samples.

Figure 6:
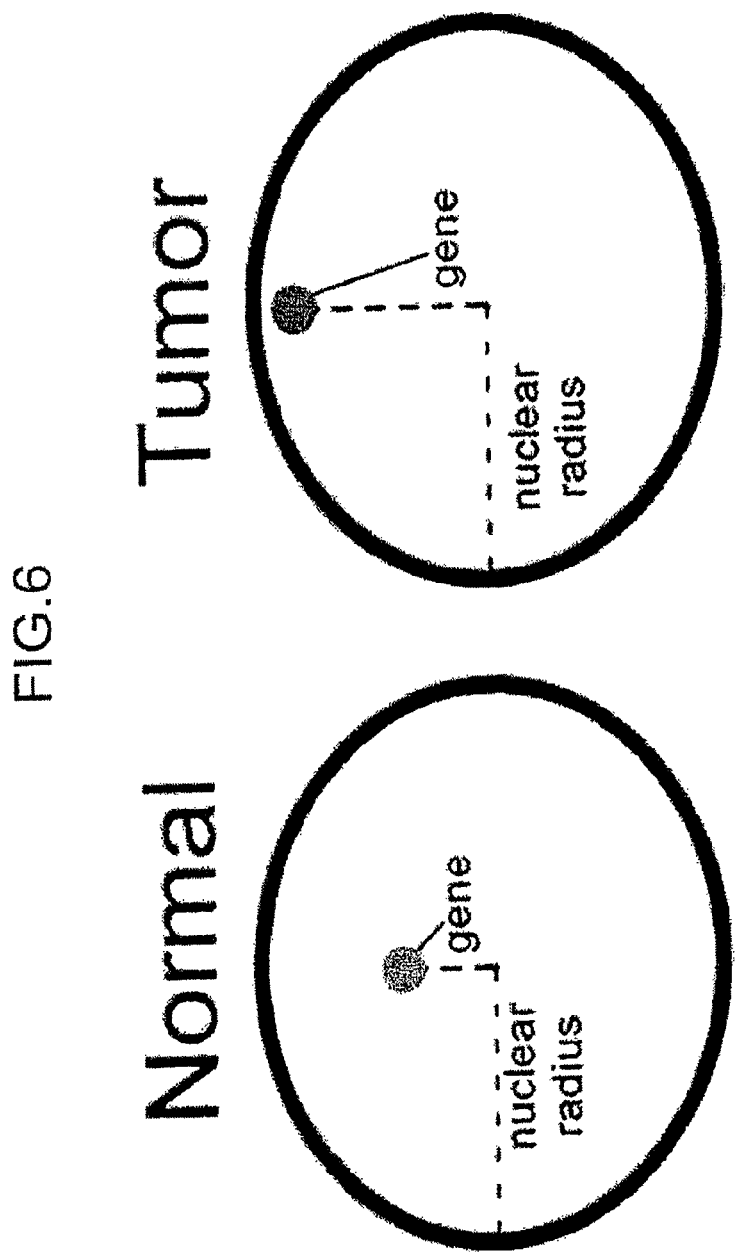

FIG. 6 conceptually depicts radial position of a gene within a nucleus of a cell.

Figure 7:
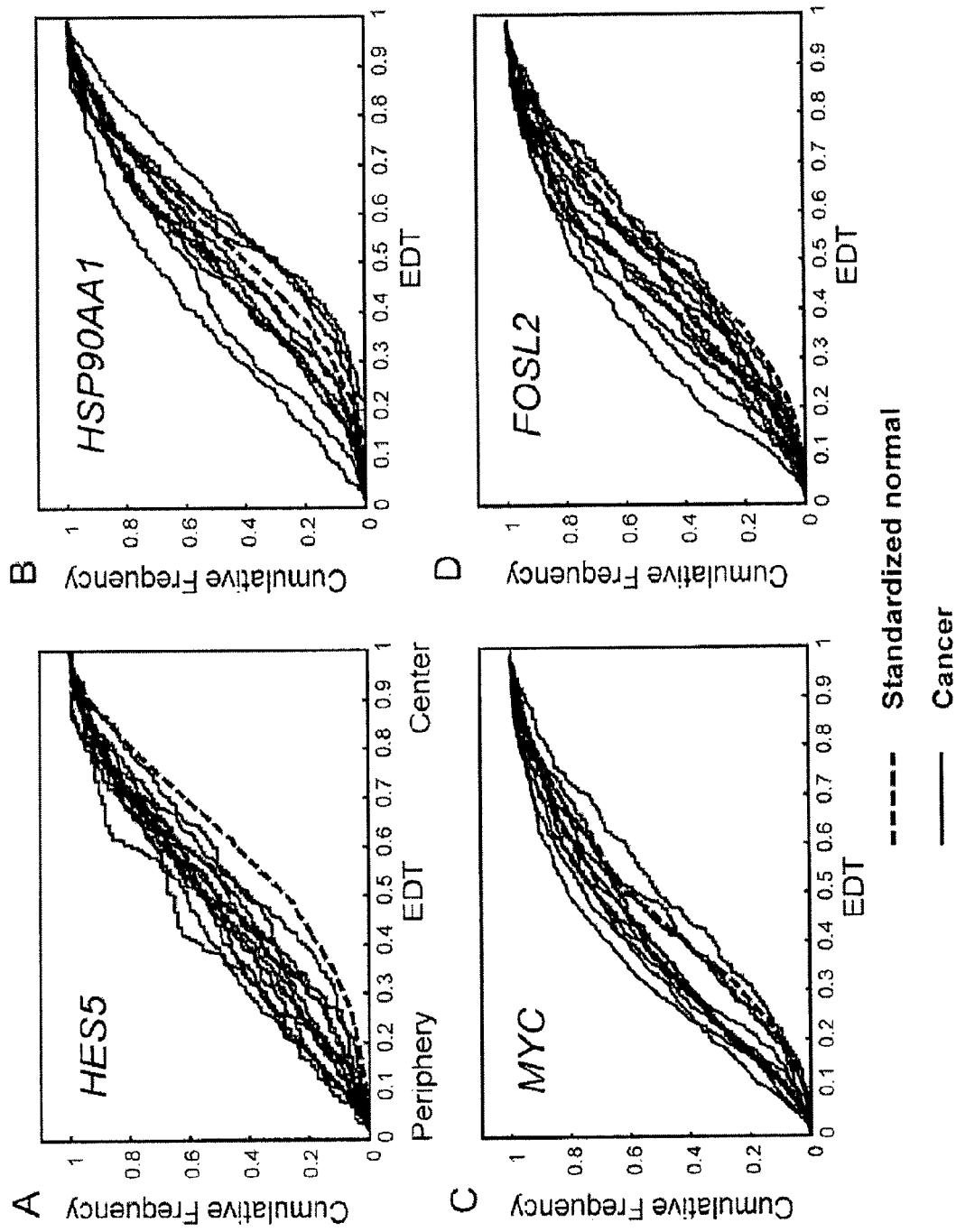

FIG. 7A is a plot of the cumulative frequency (y-axis) of the radial position (x-axis) of HES5 for the tested cancerous samples (solid lines), as compared to a standardized normal (i.e., non-cancerous) distribution (dashed line).

FIG. 7B is a plot of the cumulative frequency (y-axis) of the radial position (x-axis) of HSP90AA1 for the tested cancerous samples (solid lines), as compared to a standardized normal (i.e., non-cancerous) distribution (dashed line).

FIG. 7C is a plot of the cumulative frequency (y-axis) of the radial position (x-axis) of MYC for the tested cancerous samples (solid lines), as compared to a standardized normal (i.e., non-cancerous) distribution (dashed line).

FIG. 7D is a plot of the cumulative frequency (y-axis) of the radial position (x-axis) of FOSL2 for the tested cancerous samples (solid lines), as compared to a standardized normal (i.e., non-cancerous) distribution (dashed line).

DETAILED DESCRIPTION OF THE INVENTION

In one embodiment, the invention provides a method of detecting abnormal cells in a sample, the method comprising: (a) obtaining a sample comprising one or more cells from a subject, wherein one or more cells in the sample has a nucleus, and wherein each nucleus has a nuclear center and a nuclear membrane; (b) identifying the position of one or more genes within the nucleus relative to the nuclear center and/or nuclear membrane; and (c) comparing the position of the one or more genes with a positive and/or negative control; wherein a statistically significant difference in the position of the one or more genes as compared to a negative control, or a lack of statistically significant difference in the position of the one or more genes as compared to a positive control indicates the presence of abnormal cells.

The one or more genes can be any genes that are differentially localized in tumor tissue as compared to normal tissue. In preferred embodiments, the gene can be HES5, HSP90AA1, TGFB3, ERBB2, FOSL2 (also known as FRA2), CSF1R, MYC, AKT1 or any combination thereof. Each of these genes has been previously characterized, and sequence and other information is available through the Online Mendelian Inheritance in Man (OMIM) database (available at www.ncbi.nlm.nih.gov/sites/entrez?db=omim). Exemplary accession numbers for preferred genes can include AL139246 (HES5), M27024 (HSP90AA1), NM_003239 (TGFB3), X03363 (ERBB2), NM_005253 (FRA2/FOSL2), CSF1R (NM_005211, NM_002467 (MYC), and NM_005163 (AKT1). In more preferred embodiments, at least two genes are analyzed (i.e., identified and compared) in a given sample. However, one, two, three, four, five, six, seven, eight, or more than eight genes can be analyzed according to the methods of the present invention.

In another aspect, the invention provides a method of determining a prognosis of the subject that provided the sample in which abnormal cells have been detected. The prognosis can be determined based on comparisons of the position of one or more genes in a sample as compared with positions of genes in samples having known prognoses/phenotypes, i.e., positive controls, and/or positions of genes in normal samples, i.e., negative controls. In some cases, the control can be a standardized distribution of radial positions prepared by the methods described herein, pooling radial positions from samples having known phenotypes (i.e., normal samples, cancerous samples, cancerous samples having a specific prognosis, etc.). For example, the gene AKT1 indicates a poor prognosis when it is positioned toward the nuclear membrane or periphery as compared to a normal sample. In contrast, positioning of AKT1 toward the nuclear center as compared with a normal sample is associated with a good prognosis.

In yet another aspect, the invention provides a method for identification of gene markers for abnormal cells, the method comprising (a) obtaining a test sample comprising one or more abnormal cells from a subject, wherein one or more cells in the sample has a nucleus, and wherein each nucleus has a nuclear center and a nuclear membrane; (b) obtaining a control sample comprising one or more normal cells from a subject, wherein one or more cells in the sample has a nucleus, and wherein each nucleus has a nuclear center and a nuclear membrane; (c) identifying the position of one or more genes within the nucleus relative to the nuclear center and/or nuclear membrane; (d) comparing the position of the one or more genes from the test sample with the corresponding position of the one or more genes from the control sample; and (e) determining the statistical significance of a difference in the position of the one or more genes from the test sample as compared to the control sample; wherein a gene having a statistically significant difference in position in the test sample as compared to the control sample is identified as a gene marker for abnormal cells. In some preferred embodiments, (a)-(e) can be repeated using multiple test and/or control samples, and the resulting data pooled to provide a profile of radial positions for the one or more genes, which profile can be used as a control or a diagnostic, as shown, for example, in FIGS. 7A-7D. In more preferred embodiments, the multiple test and/or control samples are obtained from multiple subjects.

In the methods of the present invention, the abnormal cells can be any abnormal cells. Preferably, the abnormal cells are cells associated with a cancer or cancer related condition. For example, the cells can be solid tumor cells, hematologically malignant cells, benign cells, atypic cells, dysplastic cells, transformed cells, metastatic cells, non-infiltrating malignant cells, infiltrating malignant cells, pre-malignant cells, neoplastic cells, cancer stem cells, or any combination thereof, before or after a treatment has been administered. The cancer can be any cancer, including but not limited to renal cell carcinoma, hepatocellular carcinoma, cervical cancer, melanoma, thyroid carcinoma, malignant gliomas, breast cancer, colon cancer, lung cancer, pancreatic cancer, prostate cancer, stomach cancer, ovarian cancer, testicular cancer, Kaposi's sarcoma, bone cancer, B-cell lymphomas, chronic lymphocytic leukemia, acute lymphocytic leukemia, Non-Hodgkin's lymphomas, multiple myeloma, acute myelocytic leukemia, and chronic myelocytic leukemia. In another embodiment, the abnormal cells have a morphology associated with Hutchinson-Gilford Progeria.

The position of the one or more genes within the nucleus can be identified using fluorescence in situ hybridization (FISH) as described herein or using commercial FISH protocols and reagents readily available to one of ordinary skill in the art. Other methods of identifying the position of a gene in a nucleus known to one of ordinary skill in the art would also be useful in the present invention.

The position of the one or more genes within the nucleus can be identified as a percentage of the nuclear radius, i.e., the distance from the nuclear center to the nuclear membrane, also called the radial position. The nuclear center can represent 0% distance, with the nuclear membrane representing 100% distance, or alternatively, the nuclear membrane can represent 0% distance, with the nuclear center representing 100% distance. See e.g., FIG. 6. However, any other computation capable of expressing the position of a gene relative to the nuclear membrane can also be used. For example, in some embodiments the position may be measured in terms of the closest distance from the gene to the nuclear membrane, which can be measured in absolute terms, relative to the average nuclear radius, relative to the shortest nuclear radius, or relative the longest nuclear radius.

Samples for use in the methods of the present invention can be taken by any method capable of collecting cells comprising nuclei. For example, the sample can be obtained using a needle biopsy. In other embodiments, the sample can be obtained from a surgical or open biopsy. One advantage of the present invention is that samples used can be smaller than conventional biopsy samples. In a preferred embodiment, a portion of a sample obtained using a needle biopsy or surgical biopsy can be used in the methods of the present invention, while another portion of the same sample can be used in conventional diagnostic and/or prognostic methods, thereby decreasing the need for costly and/or invasive procedures in the subject. Samples can comprise a relatively small number of cells, such as about 100-250 cells. In some cases, samples can comprise fewer than about 100 cells, about 100 cells, at least 100 cells, or more than 100 cells such as 150, 200, 250, or more than 250 cells. It will be understood that the precise number of cells is not limiting. In a preferred embodiment, the sample comprises at least about 100 cells. In a more preferred embodiment, the sample comprises about 100-230 cells.

The subject can be a human or any suitable non-human mammal such as a mouse, rat, rabbit, cat, dog, pig, sheep, cow, or primate. In some embodiments, the subject is an animal used in a non-human experimental animal model, such as a mouse. In a preferred embodiment, the subject is a primate. In a more preferred embodiment, the subject is a human.

In determining statistical significance in the methods of the present invention, one of ordinary skill in the art can readily undertake the relevant calculations. Preferably, measurements will be determined at a significance of $P<0.01$. In other embodiments, measurements can be determined at a significance of $P<0.05$ or $P<0.10$. The rate of false positives and/or false negatives associated with measurement of radial position can vary by gene. For a false positive, a gene has a statistically significant (1-D KS-test, $P<0.01$) difference in radial position in a non-cancerous sample compared to that of the pooled normal distribution. A non-cancerous sample can be from any non-cancerous tissue such as normal tissue in the absence of cancer, normal tissue adjacent to cancerous tissue, and breast tissue with the non-cancerous breast diseases such as fibroadenoma and hyperplasia. For a false negative, a gene has a statistically similar radial position in a cancerous sample compared to that of the pooled normal distribution. Table 1 provides a listing of false positive and false negative rates by gene for HES5, HSP90AA1, TGFB3, ERBB2, FOSL2 (also known as FRA2), CSF1R, MYC, and AKT1.

TABLE 1

| Gene | False negatives | False positives |
| --- | --- | --- |
| HES5 | 0/13 (0%) | 1/12 (8.3%) |
| HSP90AA1 | 2/11 (18%) | 2/11 (18%) |
| TGFB3 | 3/14 (21%) | 0/13 (0%) |
| MYC | 3/11 (27%) | 0/11 (0%) |
| ERBB2 | 4/14 (29%) | 4/14 (29%) |
| FOSL2 | 4/13 (31%) | 0/12 (0%) |
| CSF1R | 4/13 (31%) | 0/12 (0%) |
| AKT1 | 5/14 (35%) | 1/12 (8.3%) |

In yet another aspect, the invention provides a kit for detecting abnormal cells in a sample, the kit comprising: (a) a labeled DNA probe for each of one or more genes selected from the group consisting of HES5, HSP90AA1, TGFB3, ERBB2, FOSL2 (also known as FRA2), CSF1R, MYC, and AKT1; and (b) instructions for measurement of the position of one or more genes in the sample, and interpretation of the results. The DNA probe can be prepared using known gene sequences for the identified genes and any suitable commercially available DNA labeling product.

The following examples further illustrate the invention but, of course, should not be construed as in any way limiting its scope.

Example 1

This example demonstrates the identification of a set of gene markers for the detection of tumor cells.

Normal and cancerous human breast tissue samples were obtained from the AIDS and Cancer Specimen Resource (ACSR), Univ. California San Francisco (UCSF), San Francisco, Calif., BioChain Institute, Inc., Hayward, Calif., Capital Biosciences, Inc, Rockville, Md., Imgenex Corp., San Diego, Calif. and US Biomax, Inc, Rockville, Md. Samples N1 through N11 were identified by the source in materials accompanying the samples as normal, i.e., non-cancerous. Samples C1 through C15 were identified as cancerous.

Samples of the tissue are prepared as formalin fixed paraffin embedded (FFPE) or FFPE tissue microarrays (TMAs). Each sample is subjected to fluorescence in situ hybridization (FISH) for twenty genes: AKT1, CSF1R, FRA2 (FOSL2), HES5, HSP90AA1, ERBB2, MYC, HES1, HEY1, MMP1/3/12, TGFB3, VEGF, ZNF217, BCL2, BRCA1, CCND1, PTGS2, PTEN, TLE, and TJP-1 (as identified in OMIM/Entrez gene).

Preparation of samples: Samples are de-paraffinated using xylene (Mallinckrodt Chemicals). A dehydrating series of ethanol at 100%-90%-70% ethanol (1×5 minutes for each) is performed, followed by 10 minutes hydration using PBS. Slides are boiled in 0.01M citrate buffer (700 ml) with a microwave for 10 minutes in 1000 watt microwave at full power (Antigen retrieval step). The samples are allowed to cool to ~37° C. Next, 10 µg/ml RNase A (Sigma)/2×SSC is added for 15 minutes at 37° C. at 1:10,000 dilution of stock, followed by 5 min PBS. One hundred µL per slide of 0.25 mg/ml proteinase K (Sigma)/2×SSC (1:100 dil 25 mg/ml stock, 1:80 dil 20 mg/ml stock) is incubated in a humidified chamber at 37° C. for: 10 minutes breast cancer sections, 11 minutes for normal breast sections, and 10 minutes 30 seconds breast TMA. Samples are quickly rinsed in PBS, followed by a dehydration ethanol series at 70%-90%-100% ethanol 1×5 minutes for each. Samples are then left to air dry.

FISH protocol: Probes are prepared using: 600-800 ng biotin (Roche) and/or digoxigenin (Roche) labeled nick translation product (commercially available probe DNA for each of the 20 genes), 10 µg human Cot1 (10 µl of 1 µg/µl stock; Roche Applied Science), 40 µg tRNA (4 µk of 10 mg/ml stock; Sigma), ¹/₁₀th volume 3M sodium acetate pH5.2, and 2× volume ice cold 100% ethanol. Probes are micro-centrifuged at max speed (~14,000 rpm) 20-25 minutes, at 4° C. The ethanol solution is decanted, and the probe is dried (air dry or using speed vac (medium, approx 10 min). The probe is resuspended in 10 µl hybridization buffer (10% dextran sulfate/50% formamide/2×SSC/1% Tween20), and allowed to rest for at least 30 minutes at room temperature. Probes are applied to tissue slides or TMA and covered with a coverslip, which is sealed. Probe and nuclei are co-denatured at 85° C. for 10 minutes and left to hybridize overnight at 37° C. in a humidified chamber. The following day, the coverslip is removed by removing the sealant and incubating in 2×SSC for 5 minutes with aggregation. Slides are washed 3× for 5 minutes in 50% formamide (Sigma)/2×SSC at 45° C., and 3× for 5 minutes in 1×SSC at 60° C. Blocking is done using 3% BSA (Sigma)/

4×SSC/0.1% Tween20 for 15 minutes at room temperature. Slides are incubated with detection reagents, which have been diluted in blocking buffer, for 2 hours at 37° C. (1:200 anti-digoxigenin-rhodamine, 1:200 fluorescein-avidin DN, both Vector Laboratories). Slides are washed in 4×SSC/ 0.1% Tween 20 for 3×5 minutes at room temperature. Slides are counterstained and mounted with Vectashield/DAPI (Vector Laboratories). Slides are stored at 4° C. until viewed on microscope.

Imaging: Slides are imaged using an Olympus IX70 microscope (Deltavision System) fitted with a CoolSnap CCD camera using a 60×, 1.4 oil objective lens and an auxiliary magnification of 1.5 and using an optical step size of 0.2 μm. The thickness of the optical section is 0.5 μm. 2D-maximal projections of entire imaging stacks are generated for analysis of FISH signal positioning.

The focal planes cover the entire nucleus. The number of sections varies depending on nucleus size. For breast tissue containing nuclei of 3-9 μm in diameter typically ~25 sections were acquired when imaging on the Olympus Deltavision system. Typically 100-230 nuclei are analyzed per gene probe.

Analysis: For the quantitative analyses of FISH signal distributions, software generated by S. Lockett and P. Gudla (National Cancer Institute, Frederick/SAIC—Frederick Inc., MD) is used. Initially images were contrast-enhanced based on visual inspection and individual cell nuclei from the blue color channel were manually delineated using the Photoshop™ program. Analysis of the red and green channels containing the signals from FISH labels was automatic as described in Meaburn et al., J. Cell Biol. 180(1): 39-50 (2008). For the automatic detection of FISH signals a three-stage process is used, involving: (i) noise reduction, (ii) segmentation and (iii) post-processing. (i) Background noise is removed in each channel by applying an adaptive non-linear noise reduction technique ("SUSAN", Smith and Brady, Int'l. J. Computer Vision 23:45-78 (1997)). (ii) A fuzzy-C-means clustering algorithm is applied on the noise-reduced images to probabilistically assign each image picture element (pixel) into two classes. The two classes correspond to background and objects in the image. The images from this process are segmented into binary images whereby each pixel with more than 50% probability of being in the object class is classified as corresponding to actual objects in the sample, while the remaining pixels are classified as background. The integrated intensities of each group of contiguous object pixels are calculated and those groups that exceed a threshold integrated intensity, which are calculated automatically by the isodata threshold method in DIPimage, are considered to correspond to individual FISH signals. Manual comparison has previously demonstrated successful identification of more than 99% of FISH signals and a false positive rate of less than 1% in a study using cultured cells (Takizawa and Misteli, Genes & Development, 22, 489-498 (2008)).

For quantification of FISH signal spatial distributions the following novel procedure was employed. For nuclei, the Euclidean distance transform (DT) is computed, where the value assigned to each pixel in a nucleus equals the shortest distance to the edge of the nucleus. These values are normalized for each nucleus such that the maximum DT value is 1.0. For each FISH signal the position of the intensity gravity center is determined and the DT value for that position is used to determine the relative radial position (RRP) of each signal.

For statistical analysis to combine the RRPs of FISH signals across multiple nuclei of the same sample, the cumulative distribution of RRPs is generated. Cumulative distributions from different samples are compared using the 1D Kolmogorov-Smirnov (KS) test and differences are consider significant if there is less than 1% probability that the two cumulative distributions arose from the same parent distribution. Pilot experiments have previously demonstrated high reproducibility between repeat experiments with variation of less than 4% of each data value. P values between repeat experiments were always more than 5%. Analysis tools are implemented using custom software written in MATLAB (Mathworks, Inc) with DIPImage toolbox (Technical University of Delft).

The relative distance of the signal between the nuclear center and the nuclear membrane, called the "radial position," of each FISH signal is determined, and data are aggregated.

Figure 1:
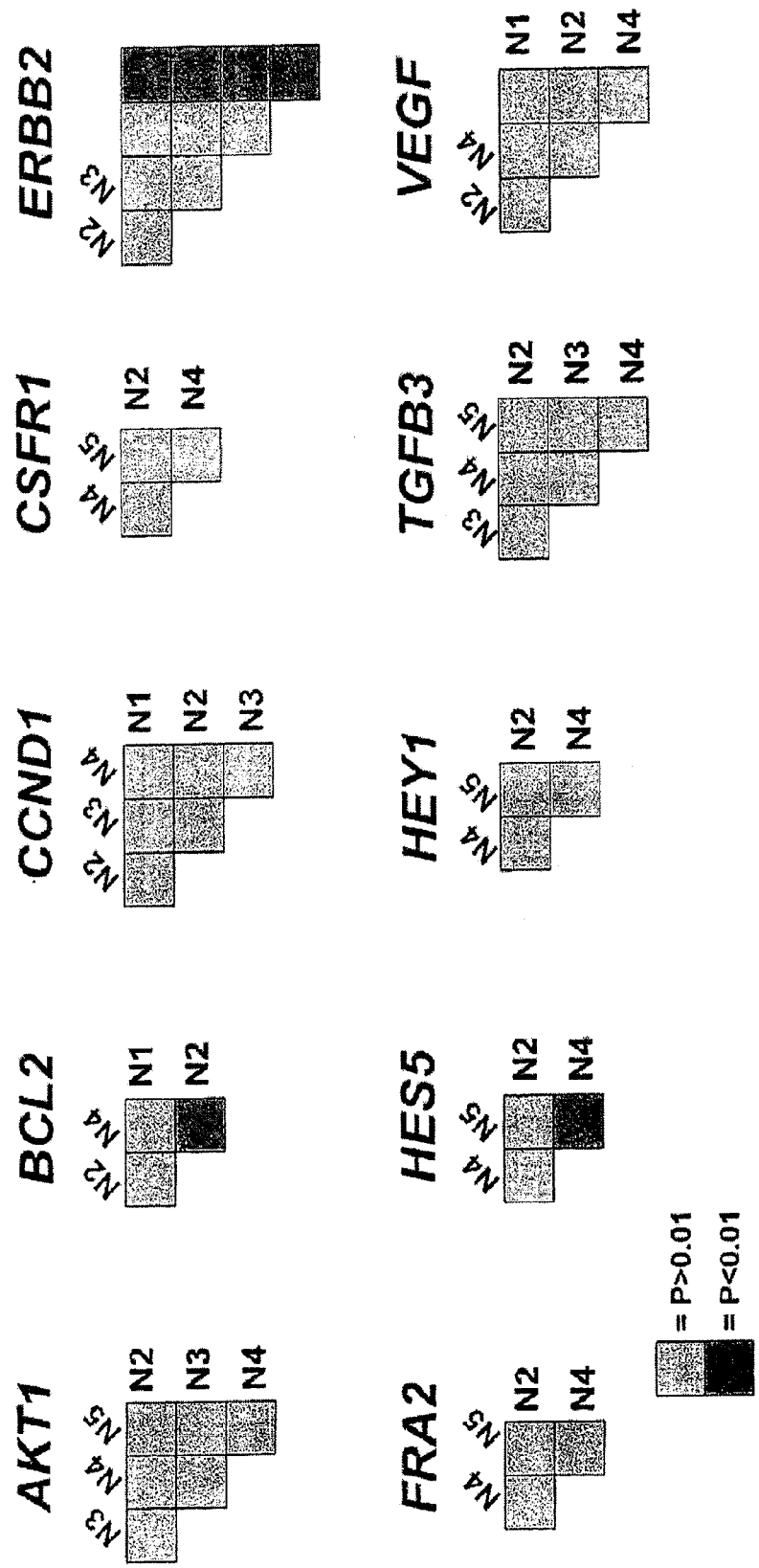

Results: Results showed little variation among control tissues in most cases. For the gene AKT1, radial positions of samples N2, N3, N4, and N5 had a consistent distribution among individuals, with P>0.01. As shown in FIG. 1, similar results were also found for BCL2, CCND1, CSFR1, ERBB2, FRA2 (FOSL2), HES5, HEY1, TGFB3, and VEGF. Most control samples, evaluated in pairs against each other, were similar to a level of P>0.01, although in analysis of ERBB2, sample N5 showed P<0.01 with respect to all other tested samples.

Figure 2:
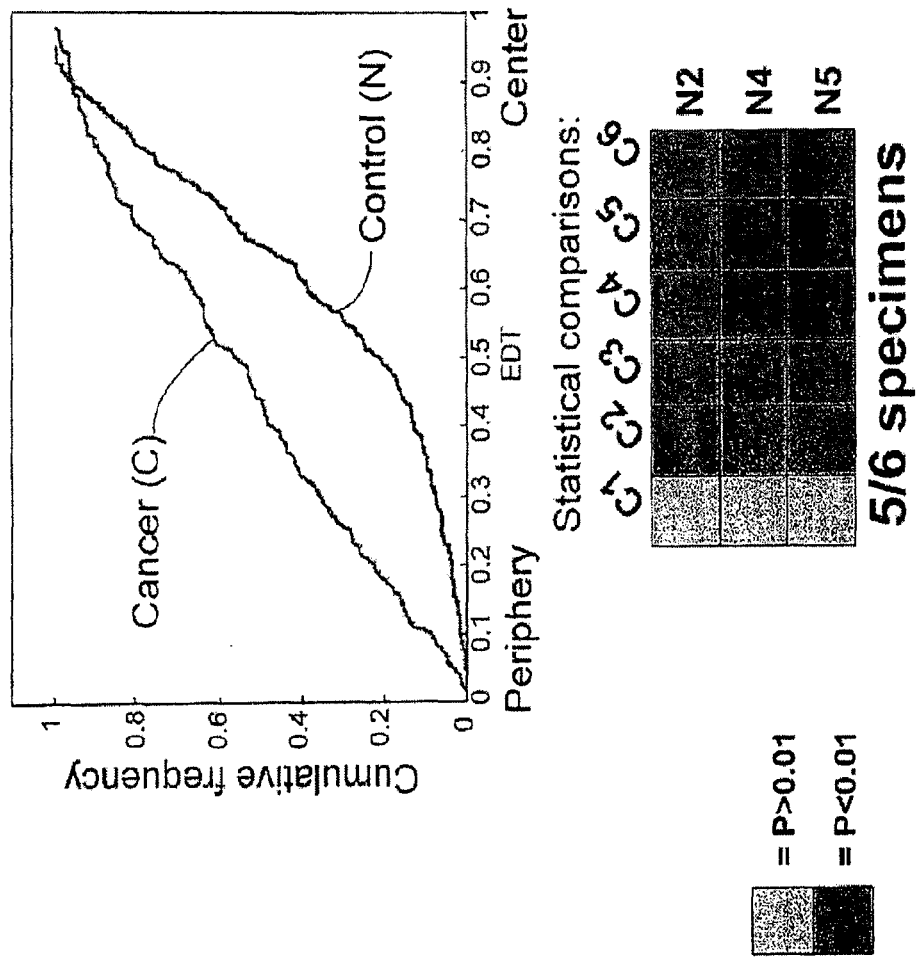
FIG. 2 is a plot of the cumulative frequency (y-axis) of the radial position (x-axis) of HES5 in an individual cancer (C) sample and an individual normal (N) sample along with statistical comparisons of six cancerous samples and three non-cancerous control samples.

When radial positions of cancer (C) samples were compared with control (N) samples, several genes showed distinction between cancer samples and control samples. In analysis of HES5, aggregated data of 5/6 cancer samples (C2-C6) showed increased location toward the periphery (nuclear membrane) as compared to control samples (FIG. 2). In analysis of AKT1 and ERBB2, aggregated data of 6/7 and 4/7 cancer samples, respectively, showed increased location toward the periphery as compared to control samples (FIG. 4).

When samples C1-C7 were quantified with respect to radial position of the twenty genes listed above, each sample had a different set of genes repositioned as compared to every other sample, as shown in Table 2 below. Radial positioning analysis of two genes, AKT1 and HES5, when considered in combination, correctly indicated cancer in all seven cancer samples. That is, for each sample, radial position of at least one of the two genes indicated cancer.

TABLE 2

| Sample | % genes repositioned |
|---|---|
| Cancer 1 | 20% (3/15) |
| Cancer 2 | 29% (4/14) |
| Cancer 3 | 70% (7/10) |
| Cancer 4 | 78% (7/9) |
| Cancer 5 | 20% (2/10) |
| Cancer 6 | 70% (7/10) |
| Cancer 7 | 53% (9/17) |

Of the twenty genes considered, at least eight of the genes were found to have radial positions useful in diagnostics: HES5, HSP90AA1, TGFB3, ERBB2, FOSL2(FRA2), CSF1R, MYC and AKT1. Table 3 below depicts P-values of the radial positions for these genes in 14 cancer samples (C1-C15) and Table 4 below depicts P-values of radial positions for these genes in 11 normal, non-cancerous samples (N1-N11). In Tables 3 and 4, "Mid-High" (P<0.01), and "High" (P<0.001) denote significantly different radial positions; "Low" (P>0.05) and "Mid-Low" (0.01<P<0.05) denote statistically similar distributions; n.d.=not determined.

TABLE 3

| C#* | HES5 | HSP90AA1 | TGFB3 | MYC | ERBB2 | FOSL2 | CSF1R | AKT1 |
|---|---|---|---|---|---|---|---|---|
| 2 | High $<1 \times 10^{-6}$ | Mid-High 0.0042 | Low 0.281 | n.d. | High $3 \times 10^{-6}$ | Low 0.516 | Mid-High 0.0079 | High $4.4 \times 10^{-4}$ |
| 3 | High $<1 \times 10^{-6}$ | High $<1 \times 10^{-6}$ | High $4.6 \times 10^{-4}$ | High $<1 \times 10^{-6}$ | Mid-High 0.0012 | High $<1 \times 10^{-6}$ | High $4 \times 10^{-6}$ | High $1.7 \times 10^{-4}$ |
| 4 | High $<1 \times 10^{-6}$ | High $<1 \times 10^{-6}$ | High $<1 \times 10^{-6}$ | High $<1 \times 10^{-6}$ | High $<1 \times 10^{-6}$ | n.d. | n.d. | High $1.6 \times 10^{-5}$ |
| 5 | High $<1 \times 10^{-6}$ | High $7.0 \times 10^{-5}$ | High $6.1 \times 10^{-4}$ | Low 0.860 | Low 0.060 | Mid-Low 0.028 | Low 0.190 | Low 0.513 |
| 6 | High $<1 \times 10^{-6}$ | n.d. | Mid-High 0.0021 | n.d. | Mid-High 0.0043 | High $<1 \times 10^{-6}$ | Mid-Low 0.025 | High $5 \times 10^{-6}$ |
| 7 | n.d. | n.d. | High $<1 \times 10^{-6}$ | n.d. | High $<1 \times 10^{-6}$ | High $<1 \times 10^{-6}$ | High $<1 \times 10^{-6}$ | High $<1 \times 10^{-6}$ |
| 8 | High $<1 \times 10^{-6}$ | High $2.2 \times 10^{-4}$ | High $<1 \times 10^{-6}$ | High $<1 \times 10^{-6}$ | High $<1 \times 10^{-6}$ | Mid-High 0.0066 | High $<1 \times 10^{-6}$ | Low 0.282 |
| 9 | High $<1 \times 10^{-6}$ | High $7 \times 10^{-6}$ | High $<1 \times 10^{-6}$ | High $<1 \times 10^{-6}$ | High $<1 \times 10^{-6}$ | High $<1 \times 10^{-6}$ | High $<1 \times 10^{-6}$ | High $2.1 \times 10^{-5}$ |
| 10 | High $<1 \times 10^{-6}$ | Low 0.094 | High $8.9 \times 10^{-4}$ | High $<1 \times 10^{-6}$ | High $<1 \times 10^{-6}$ | Low 0.077 | High $4 \times 10^{-6}$ | Low 0.064 |
| 11 | Mid-High 0.0013 | High $1.3 \times 10^{-5}$ | Mid-High 0.0039 | Mid-Low 0.019 | Low 0.242 | High $3 \times 10^{-6}$ | Low 0.095 | High $<1 \times 10^{-6}$ |
| 12 | High $<1 \times 10^{-6}$ | Mid-High 0.0071 | High $7 \times 10^{-6}$ | High $<1 \times 10^{-6}$ | High $3.4 \times 10^{-4}$ | High $1.3 \times 10^{-4}$ | High $<1 \times 10^{-6}$ | High $8.8 \times 10^{-4}$ |
| 13 | Mid-High 0.0012 | Mid-Low 0.049 | Low 0.987 | High $<1 \times 10^{-6}$ | High $<1 \times 10^{-6}$ | High $<1 \times 10^{-6}$ | High $5.2 \times 10^{-4}$ | Low 0.384 |
| 14 | High $2.6 \times 10^{-5}$ | Mid-High 0.0070 | Mid-High 0.0073 | High $<1 \times 10^{-6}$ | Low 0.063 | Low 0.424 | Mid-Low 0.019 | Low 0.143 |
| 15 | High $<1 \times 10^{-6}$ | n.d. | Low 0.099 | Low 0.364 | Low 0.067 | High $<1 \times 10^{-6}$ | High $<1 \times 10^{-6}$ | High $<1 \times 10^{-6}$ |

*C# = Cancer sample

TABLE 4

| N#* | HES5 | HSP90AA1 | TGFB3 | MYC | ERBB2 | FOSL2 | CSF1R | AKT1 |
|---|---|---|---|---|---|---|---|---|
| 1 | Low** 0.766 | Low 0.220 | Low 0.633 | Low 0.949 | Low 0.767 | Low 0.915 | Low 0.390 | Low 0.596 |
| 2 | Low 0.498 | Low 0.997 | n.d. | n.d. | n.d. | Low 0.285 | Low 0.058 | n.d. |
| 3 | Low 0.954 | Low 0.914 | Low 0.151 | Low 0.276 | Mid-Low 0.022 | n.d. | n.d. | Mid-Low 0.037 |
| 4 | n.d. | n.d. | n.d. | n.d. | Low 0.342 | n.d. | n.d. | n.d. |
| 5 | Low 0.969 | n.d. | Low 0.701 | Low 0.998 | Low 0.555 | Low 0.112 | Low 0.917 | Mid-High 0.0014 |
| 6 | n.d. | n.d. | Low 0.353 | Low 0.325 | Low 0.981 | n.d. | Low 0.315 | N/A |
| 7 | n.d. | Low 0.967 | n.d. | n.d. | n.d. | Low 0.656 | n.d. | n.d. |
| 8 | Low 0.763 | Low 0.081 | Low 0.543 | Low 0.178 | Low 0.129 | Low 0.579 | Low 0.158 | Low 0.144 |
| 9 | n.d. | n.d. | Low 0.673 | n.d. | Low 0.510 | n.d. | n.d. | Low 0.873 |
| 10 | Low 0.116 | Low 0.889 | Low 0.133 | 0.694 | Low 0.995 | Low 0.062 | Low 0.083 | Low 0.924 |
| 11 | Low 0.133 | n.d. | Low 0.297 | n.d. | Mid-High 0.0011 | Low 0.687 | Low 0.569 | Low 0.652 |

*N# = Normal, i.e., non-cancerous sample

Five of the genes were identified as having small repositioning events: HES1, HEY1, MMP1/3/12, VEGF, and ZNF217. The remaining seven genes were found either not to be repositioned in cancer as compared to normal cells, or to have limited repositioning in a minority of samples: BCL2, BRCA1, CCND1, PTGS2, PTEN, TLE, and TJP-1. Differences in radial position were not associated with aneuploidy.

These results demonstrate that gene markers for cancerous cells can be identified using radial position.

Example 2

This example demonstrates the use of spatial gene positioning analysis in vitro to correlate prognosis in a subject to radial position of a gene.

Figure 3:
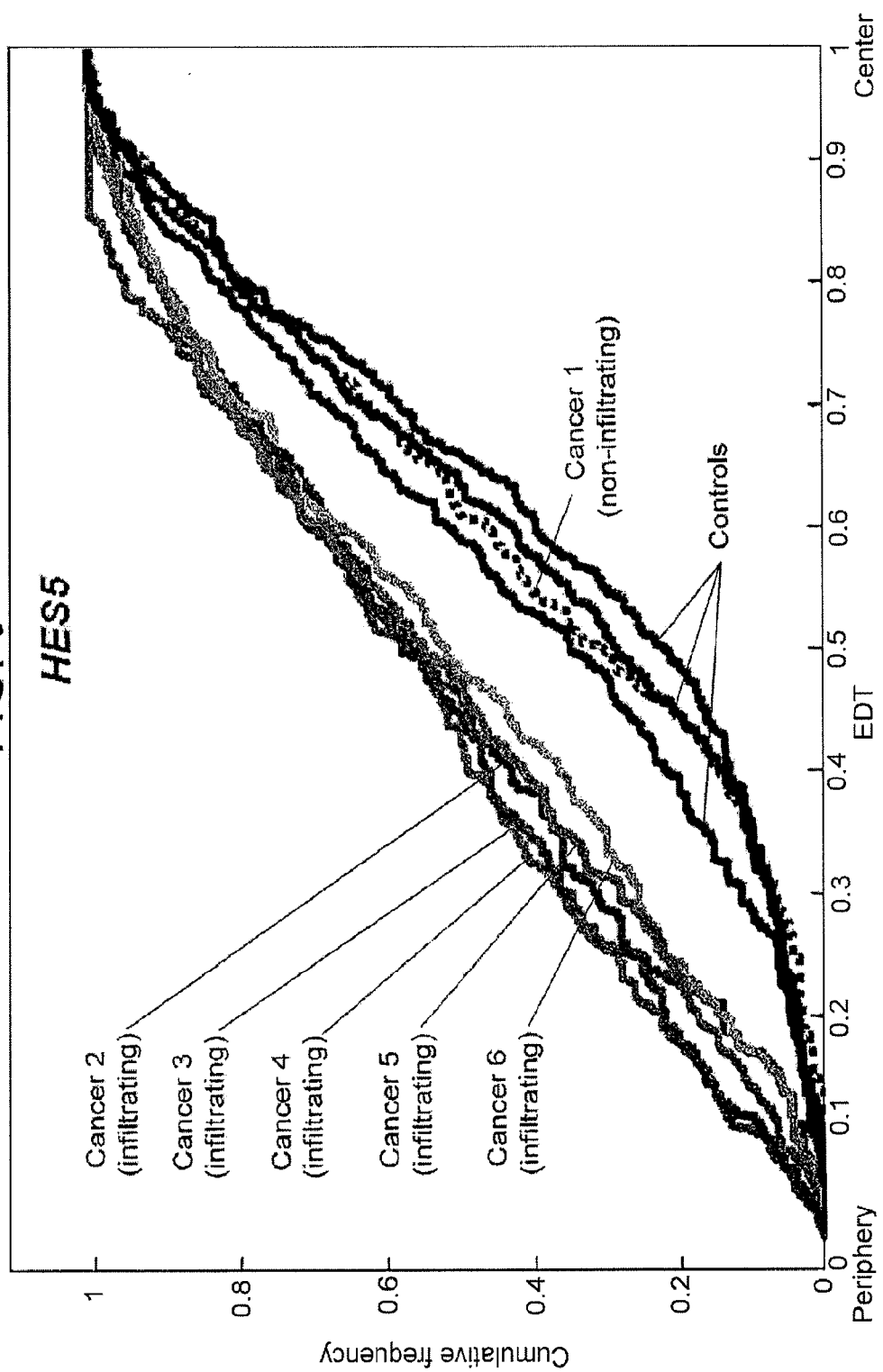
FIG. 3 is a plot of the cumulative frequency (y-axis) of the radial position (x-axis) of HES5 for six cancerous samples and three non-cancerous control samples. Samples C2-C6 are depicted in a common positional group, while sample C1 is shown separately due to its alignment with the control samples.

FISH imaging and analysis were carried out as described in Example 1 with respect to cancerous samples C1-C7 and control samples N1-N5. Aggregated analysis showed that HES5 positioning was highly correlated among cancerous samples C2-C6, and highly correlated among control samples N1-N5, as shown in FIG. 3. However, individual analysis of C1-C6 as compared to control (N) samples showed that the radial position of HES5 in C1 was aligned with the control samples (FIG. 3). The phenotype of the cancer of C1 was separately described as less aggressive than C2-C6 in materials accompanying the tissue samples, which were provided by ACSR (UCSF, San Francisco, Calif.)

In analysis of AKT1 positioning, several cancerous samples (C3, C4, C6, C7) showed increased location toward the periphery as compared to the control samples (FIG. 5). These samples were identified as having aggressive phenotypes, i.e., poor prognosis. Other cancerous samples (C1, C2) showed increased location toward the nuclear center as compared to the control samples. These samples were identified as having less aggressive phenotypes, i.e., good prognosis. Sample C5 showed similar location as compared to the control samples, with respect to AKT1. In materials provided by ACSR (UCSF, San Francisco, Calif.) accompanying the cell samples, it was noted that sample C5 had well characterized cellular markers of both good (estrogen receptor positive and progesterone receptor positive) and poor prognosis (Epidermal growth factor receptor 2 positive).

These results show that radial position of a gene in a sample can provide basis for prognosis, based on comparison with negative controls and samples having known phenotypes.

Example 3

This example demonstrates the use of spatial gene positioning analysis to diagnose cancer in a patient.

A first sample is obtained from a patient A using a needle biopsy. A second sample is obtained from patient B using a needle biopsy. The two samples are prepared and evaluated as described in Example 1, using HES5, HSP90AA1, TGFB3, ERBB2, FOSL2 (FRA2), CSF1R, MYC and AKT1 or a subset of at least two of these genes. The radial position of each selected gene is evaluated using FISH, and compared to a non-cancerous control sample. The radial position of each selected gene is then compared to a positive control, such as a cancerous sample or a profile of radial positions previously prepared. For example, the profile can be a standardized distribution of the gene in the analyzed tissue previously generated by pooling gene positioning data from a large pool (typically 10-20 tissue samples) of normal tissues.

For the sample taken from patient A, the radial position of at least one of the selected genes in the sample is statistically significantly different from the position of the corresponding genes of the non-cancerous sample, i.e., negative control.

For the sample taken from patient B, the radial position of at least one of the selected genes is found to be similar to that of the positive control.

These results indicate a diagnosis of cancer, which is able to be confirmed by standard cancer diagnostics.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting a peripheral position of the HES5 gene in cells in a breast tissue sample from a human subject, the method comprising:
   (a) obtaining a breast tissue sample comprising one or more cells from the subject, wherein one or more cells in the breast tissue sample has a nucleus, and wherein each nucleus has a nuclear center and a nuclear membrane;
   (b) contacting the breast tissue sample with a labeled DNA probe;
   (c) hybridizing the labeled DNA probe with the HES5 gene by fluorescence in situ hybridization (FISH);
   (d) providing a positive and/or negative control; and
   (e) detecting a peripheral position of the HES5 gene within the nucleus relative to the nuclear center and/or nuclear membrane by FISH with the labeled DNA probe, wherein the peripheral position of the HES5 gene is:

(i) a statistical difference between the position of the HES5 gene in the breast tissue sample and the nuclear center position of the HES5 gene in the negative control; and/or
(ii) a lack of a statistical difference between the position of the HES5 gene in the breast tissue sample and the peripheral position of the HES5 gene in the positive control.

2. The method of claim 1, further comprising detecting a peripheral position of one or more of HSP90AA1, FOSL2, CSF1R, MYC, TGFB3, ERBB2, and AKT1 genes within the nucleus relative to the nuclear center and/or nuclear membrane by FISH, wherein the peripheral position is:
(i) a statistical difference between the position of one or more of the HSP90AA1, FOSL2, CSF1R, MYC, TGFB3, ERBB2, and AKT1 genes in the breast tissue sample and the nuclear center position of the respective one or more genes in the negative control; and/or
(ii) a lack of a statistical difference between the position of one or more of the HSP90AA1, FOSL2, CSF1R, MYC, TGFB3, ERBB2, and AKT1 genes in the breast tissue sample and the peripheral position of the respective one or more genes in the positive control.

3. The method of claim 2, further comprising
detecting an increased proximity to the nuclear membrane of (i) the HES5 gene and (ii) one or more of the HSP90AA1, FOSL2, CSF1R, MYC, TGFB3, ERBB2, and AKT1 genes in the breast tissue sample relative to the proximity to the nuclear membrane of (i) the HES5 gene and (ii) the respective one or more genes in the negative control.

4. The method of claim 2, wherein the breast tissue sample is obtained using a needle biopsy.

5. The method of claim 2, wherein the positive control is a standardized distribution profile of the position of (i) the HES5 gene and (ii) one or more of the HSP90AA1, FOSL2, CSF1R, MYC, TGFB3, ERBB2, and AKT1 genes in a breast cancer control sample and the negative control is a standardized distribution profile of the position of (i) the HES5 gene and (ii) one or more of the HSP90AA1, FOSL2, CSF1R, MYC, TGFB3, ERBB2, and AKT1 genes in a non-cancerous control sample from breast tissue.

6. The method of claim 2, comprising detecting the positions within the nucleus relative to the nuclear center and/or nuclear membrane of the following:
(a) HES5 and HSP90AA1,
(b) HES5 and FOSL2,
(c) HES5 and CSF1R, or
(d) HES5 and MYC.

7. The method of claim 2, comprising detecting the positions within the nucleus relative to the nuclear center and/or nuclear membrane of the following:
(a) HES5 and TGFB3,
(b) HES5 and ERBB2, or
(c) HES5 and AKT1.

8. The method of claim 2, comprising detecting the positions within the nucleus relative to the nuclear center and/or nuclear membrane of (i) the HES5 gene and (ii) two or more of the HSP90AA1, FOSL2, CSF1R, MYC, TGFB3, ERBB2, and AKT1 genes by FISH.

9. The method of claim 8, comprising detecting the positions within the nucleus relative to the nuclear center and/or nuclear membrane of the HES5, TGFB3, and FOSL2 genes.

10. The method of claim 8, wherein the statistical difference between the positions of (i) the HES5 gene and one or more of the HSP90AA1, FOSL2, CSF1R, MYC, TGFB3, ERBB2, and AKT1 genes in the breast tissue and (ii) the nuclear center positions of the HES5 gene and the respective one or more genes in the negative control is a P-value of $P<0.01$.

11. The method of claim 2, wherein the statistical difference between the positions of (i) the HES5 gene and one or more of the HSP90AA1, FOSL2, CSF1R, MYC, TGFB3, ERBB2, and AKT1 genes in the breast tissue sample and (ii) the nuclear center positions of the HES5 genes and the respective one or more genes in the negative control is a P-value of $P<0.01$.

12. The method of claim 2, comprising detecting an increased proximity to the nuclear center of (i) the HES5 gene and (ii) one or more of the HSP90AA1, FOSL2, CSF1R, MYC, TGFB3, ERBB2, and AKT1 genes in the breast tissue sample relative to the proximity to the nuclear membrane of (i) the HES5 gene and the (ii) the respective one or more genes in the positive control.

13. The method of claim 1, further comprising
detecting an increased proximity to the nuclear membrane of the HES5 gene in the breast tissue sample relative to the proximity to the nuclear membrane of the HES5 gene in the negative control.

14. The method of claim 1, wherein the breast tissue sample is obtained using a needle biopsy.

15. The method of claim 1, wherein the positive control is a standardized distribution profile of the position of the HES5 gene in a breast cancer control sample and the negative control is a standardized distribution profile of the position of the HES5 gene in a non-cancerous control sample from breast tissue.

16. The method of claim 1, wherein the statistical difference between the position of the HES5 gene in the breast tissue sample and the nuclear center position of the HES5 gene in the negative control is a P-value of $P<0.01$.

17. The method of claim 1, further comprising treating cancer in the subject.

18. The method of claim 1, comprising detecting an increased proximity to the nuclear center of the HES5 gene in the breast tissue sample relative to the proximity to the nuclear membrane of the HES5 gene in the positive control.

* * * * *

UNITED STATES PATENT AND TRADEMARK OFFICE
CERTIFICATE OF CORRECTION

PATENT NO. : 9,617,599 B2  
APPLICATION NO. : 13/062247  
DATED : April 11, 2017  
INVENTOR(S) : Thomas A. Misteli and Karen Meaburn It is certified that error appears in the above-identified patent and that said Letters Patent is hereby corrected as shown below:

At Column 1, Line 13, above the heading "BACKGROUND OF THE INVENTION" please insert the following heading and paragraph:

--STATEMENT REGARDING FEDERALLY SPONSORED RESEARCH AND DEVELOPMENT  
This invention was made with government support under W81XWH-08-2-0098 awarded by Department of Defense, Medical Research and Materiel Command (MRMC). The government has certain rights in the invention.--

Signed and Sealed this  
Ninth Day of April, 2019

Andrei Iancu  
*Director of the United States Patent and Trademark Office*